United States Patent [19]

Gloskey

[11] Patent Number: 4,658,046
[45] Date of Patent: Apr. 14, 1987

[54] PROCESS FOR THE PREPARATION OF METHYLTIN CHLORIDES

[75] Inventor: Carl R. Gloskey, Hilton Head Island, S.C.

[73] Assignee: Zemex Corporation, New York, N.Y.

[21] Appl. No.: 752,795

[22] Filed: Jul. 8, 1985

[51] Int. Cl.$^4$ .............................................. C07F 7/22
[52] U.S. Cl. .................................................. 556/100
[58] Field of Search ........................................ 556/100

[56] References Cited

U.S. PATENT DOCUMENTS

| | | | |
|---|---|---|---|
| 3,519,665 | 7/1970 | Molt et al. ............................ | 556/100 |
| 3,745,183 | 7/1973 | Katsumura et al. ............. | 556/100 X |
| 3,872,143 | 3/1975 | Boboli et al. ......................... | 556/100 |
| 3,975,417 | 8/1976 | Sagawa et al. ....................... | 556/100 |
| 4,052,426 | 10/1977 | Wehner et al. ..................... | 556/100 |
| 4,092,340 | 5/1978 | Jones ................................. | 556/100 X |

FOREIGN PATENT DOCUMENTS

| | | |
|---|---|---|
| 3617 | 3/1966 | Japan . |
| 41337 | 10/1972 | Japan . |
| 719733 | 12/1954 | United Kingdom . |
| 1053996 | 1/1967 | United Kingdom . |

*Primary Examiner*—Helen M. S. Sneed

[57] ABSTRACT

Methyltin trichloride and dimethyltin dichloride are prepared in high yields without pressure using pentavalent organophosphorous dihalides as a catalyst. The catalyst may be reused for multiple sequential preparations of the methyltin chlorides.

5 Claims, No Drawings

PROCESS FOR THE PREPARATION OF METHYLTIN CHLORIDES

This invention involves the preparation of methyltin chlorides without pressure using a pentavalent phosphorous compound as a catalyst. Methyltin chlorides such as methyltin trichloride and dimethyltin dichloride are used in large quantities for the surface treatment of glass and as intermediates for the manufacture of methyltin stabilizers for polyvinyl chloride.

Many processes are known to produce the methyltin chlorides; however, those of practical commercial value involve the reaction of chloromethane and tin along with a catalyst.

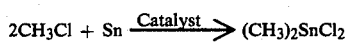

$$2CH_3Cl + Sn \xrightarrow{Catalyst} (CH_3)_2SnCl_2$$

U.S. Pat. No. 3,857,868 discloses a process which requires high pressure, preferably 200 p.s.i.g., and three preferred catalysts:
(a) tetraalkyl ammonium chloride $R_4NCl$
(b) tetraalkyl ammonium trichlorostannite $R_4NSnCl_3$
(c) trialkyl amine $R_3N$ U.S. Pat. No. 3,901,824 discloses a process using a catalyst comprised of tin tetrachloride and at least one compound selected from tributyl amine, methyl tributyl phosphonium chloride and methyl tributyl ammonium chloride. Typically this reaction is reported to take 12–18 hours. Example 11 of this patent shows that tributyl phosphorous does not work as a catalyst and in Example 20 the use of stannous chloride and tributylphosphorous produced yield less than 25% after 16 hours.

U.S. Pat. No. 3,792,059 involves the use of an onium catalyst such as tributylmethyl phosphonium iodide.

U.S. Pat. No. 3,415,857 discloses the use of alkyl bromides reacted with tin using stannous bromide and a catalyst based on quaternary ammonium or quaternary phosphonium chloride or bromides plus the salt of one of various metals.

U.S. Pat. No. 3,519,665 claims a process using a catalyst based on ammonium or phosphonium iodides.

U.S. Pat. No. 3,340,283 discloses a method of preparing methyltin trichloride from stannous chloride using an amine catalyst.

It has now been discovered that methyltin chlorides such as methyltin trichloride and dimethyltin dichloride can be prepared in 3 hours using no pressure, avoiding suspected carcinogenic iodides, and eliminating the alkyl quaternary phosphonium or ammonium compounds or trivalent phosphines or amines.

The process of this invention involves a pentavalent organophosphorous salt such as tributylphosphorous dichloride or tributylphosphorous dibromide as a catalyst. Tin may be used in the form of sponge, powder, chips, molten, or foil. The reaction is best carried on with tin chips. If methyltin trichloride is desired, stannous chloride may be substituted for the tin.

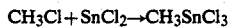

$$CH_3Cl + SnCl_2 \rightarrow CH_3SnCl_3$$

Also, mixtures of tin and stannous chloride may be used if the desired product is a mixture of methyltin trichloride and dimethyltin dichloride which is preferred for the manufacture of methyltin mercaptides, salts, or esters used in polyvinyl chloride stabilization.

The triorganophosphorous dihalide may be prepared by low temperature reaction of chlorine or bromine with a triorganophosphorous or by reduction with metallic halides such as antimony pentachloride.

An example of the invention to prepare mixed methyltin chlorides are intermediates for polyvinyl chloride stabilizers but not limited to the named reactants follows:

EXAMPLE #1

A 1000 ml three neck flask is fitted with a methyl chloride inlet tube, a high speed agitator, a reflux condenser, and a thermometer. The flask is enclosed in an electric heating mantle.

The flask may be charged with 273.2 g (1 mol) of tributylphosphorous dichloride; 118.7 g (1 mol) of tin chips; 189.6 g (1 mol) of stannous chloride. The flask contents may be heated to 185°–190° C. and methyl chloride added until the solids disappear and no further methyl chloride is utilized as evidenced by its escape from the flask and bubbles appearing in a water chamber connected to the vent. The total reaction took 2 hours and 27 minutes.

The methyltin trichloride-dimethyltin dichloride may be recovered by removing the reflux condenser and connecting the reactor flask with a non-packed column wrapped with a heating tape to a 500 ml flask and reducing the pressure in the receiver to 50 mm Hg pressure. When the distillation was completed at 40 mm pressure and 200° C., the system was shut down.

An additional 118.7 g of tin was added to the flask and the process repeated reacting methyl chloride with the tin at 185°–190° C. for 2½–3 hours. This process was again repeated until 4 cycles were completed. The overall yield was in excess of 90% containing a mixture of about 82% dimethyltin dichloride and 18% methyltin trichloride. The reactor flask residue contained some complexed methyltin chloride and catalyst which can be further recycled.

EXAMPLE #2

1 mol (202 g) of dimethyltin dichloride prepared by the method of Example #1 was dissolved in 2 mols (408 g) of isooctylmercapto acetate. To this solution in a 2000 ml beaker a 20% aqueous solution of 100 g of sodium carbonate was added slowly with mechanical agitation. The rate of addition was such to avoid foaming overflow from liberated $CO_2$. This addition took about 15 minutes. The mixture was then heated to 60° C. for 30 minutes and the aqueous phase containing sodium chloride was separated. The product dimethyltin bis(isooctylmercapto acetate) was heated to 115° C. for 5 minutes to remove residual water then cooled and filtered. The yield was 99% of theory.

The dimethyltin bis(isooctylmercapto acetate) was used as a stabilizer in a polyvinyl chloride brabender test and compared with dibutyltin bis(isooctylmercapto acetate). The methyltin stabilizer on equal weight basis was about 10% more efficient than the butyltin stabilizer and equivalent to the butyltin performance when based on equal tin content.

What I claim is:

1. A process for the preparation of methyltin chlorides by reacting methyl chloride with metallic tin and/or stannous chloride in the presence of a pentavalent organophosphorous dihalide at a temperature of 200°

C.±15° C. and recovering the methyltin chlorides by vacuum distillation, solvent recrystallization, aqueous hydrolysis, or by using the product directly to make mercaptides or organotin esters useful for polyvinyl chloride stabilization.

2. The process of claim 1 wherein the catalyst is tributylphosphorous dichloride.

3. The process of claim 1 wherein the catalyst is a triorganophosphorous dichloride.

4. The process of claim 1 wherein the catalyst is a triorganophosphorous dibromide.

5. The process of claim 1 wherein the mol ratio of Sn to $SnCl_2$ may range from 0–10 or 10–0.

* * * * *